(12) United States Patent
Kahn et al.

(10) Patent No.: US 11,297,791 B2
(45) Date of Patent: *Apr. 12, 2022

(54) CANNABIS PLANT NAMED 'V3'

(71) Applicant: GenCann, LLC, Ukiah, CA (US)

(72) Inventors: Mikah Kahn, New York, NY (US); Brent Kaiser, Laytonville, CA (US); Blake Borges, Laytonville, CA (US); Michael Nazarian, Laytonville, CA (US); Justin Eric Delong, Laytonville, CA (US)

(73) Assignee: GenCann, LLC, Laytonville, CA (US)

( * ) Notice: Subject to any disclaimer, the term of this patent is extended or adjusted under 35 U.S.C. 154(b) by 11 days.

This patent is subject to a terminal disclaimer.

(21) Appl. No.: 16/846,178

(22) Filed: Apr. 10, 2020

(65) Prior Publication Data

US 2020/0323164 A1 Oct. 15, 2020

Related U.S. Application Data

(60) Provisional application No. 62/832,863, filed on Apr. 11, 2019.

(51) Int. Cl.
*A01H 6/28* (2018.01)
*A01H 5/12* (2018.01)
*A61K 36/185* (2006.01)

(52) U.S. Cl.
CPC ............... *A01H 6/28* (2018.05); *A01H 5/12* (2013.01); *A61K 36/185* (2013.01)

(58) Field of Classification Search
CPC ........................................................ A01H 6/28
USPC ........................................................ Plt./258
See application file for complete search history.

(56) References Cited

U.S. PATENT DOCUMENTS

| | | | | |
|---|---|---|---|---|
| PP33,210 P3 * | 6/2021 | Kahn | ............ | A01H 5/02 Plt./258 |
| PP33,211 P3 * | 6/2021 | Kahn | ............ | A01H 5/12 Plt./258 |
| PP33,212 P3 * | 6/2021 | Kahn | ............ | A01H 5/02 Plt./258 |

OTHER PUBLICATIONS

Hazekamp, Arno, Katerina Tejkalová, and Stelios Papadimitriou. "Cannabis: from cultivar to chemovar II—a metabolomics approach to Cannabis classification." Cannabis and Cannabinoid Research 1.1 (2016): 202-215. (Year: 2016).*

* cited by examiner

*Primary Examiner* — Weihua Fan
(74) *Attorney, Agent, or Firm* — Plant & Planet Law Firm

(57) ABSTRACT

The unique annual herbaceous cannabis plant variety *C. sativa* 'V3' is provided. The variety can be distinguished by its outstanding features of increased production of tetrahydrocannabivarin. The enhanced production of THCV inhibits the stimulation to eat normally associated with tetrahydrocannabinol.

6 Claims, 5 Drawing Sheets

CANNABIS PLANT NAMED 'V3'

CROSS REFERENCE TO RELATED APPLICATIONS

This application claims the benefit of U.S. Provisional Application No. 62/832,863 filed on Apr. 11, 2019, which is incorporated herein by reference in its entirety as though fully set forth herein.

BACKGROUND OF THE INVENTION

Field of the Invention

The present invention relates to a new and distinct annual variety of *C. sativa* hybrid, which has been given the variety denomination of 'V3'. 'V3' is intended for use as medicinal herb for sale in cannabis dispensaries and for use in the manufacture of medicinal and recreational products.

Background of the Related Art

The genus *Cannabis* has been in use by humans for millennia, due to the multiplicity of its benefits to humans, including the considerable value and utility of its fiber, the nutritional value of its seeds, and the medicinal value of its floral parts and products made from them. Currently the genus is under intense legal commercialization in the United States as industrial hemp for a variety of purposes including biodegradable plastics and building materials, clothing, paper, food, fuel and medicines.

Cannabidiol (CBD) extracted from *Cannabis* is widely used in over-the-counter medicines and topical treatments, and is also the active ingredient in the FDA-approved drug Epidiolex. CBD is just one of at least dozens—perhaps hundreds—of cannabinoids endogenous to *Cannabis,* tetrahydrocannabinol (THC) being the other cannabinoid that is most well-known. The cannabinoids as a group interact with the human endocannabinoid receptors, which are distributed in the brain and throughout the body. The study of the endocannabinoid system (ECS) in humans and other mammals is an area of increasing interest and holds tremendous promise for the future of medicine. See, e.g., Russo (2019). Cannabis and Pain, *Pain Medicine,* 20(10): 1093/pm/pnz227; and Russo (2016). Clinical Endocannabinoid Deficiency Reconsidered: Current Research Supports the Theory in Migraine, Fibromyalgia, Irritable Bowel, and Other Treatment-Resistant Syndromes, *Cannabis Cannabinoid Res.* 1(1): 154-165.

Non-hemp forms of *Cannabis,* frequently referred to as marijuana, have been legalized for medicinal use in many states and also for recreational use (sometimes called "adult use") in a growing number of states and including Alaska, California, Colorado, Illinois, Maine, Massachusetts, Nevada, Oregon, Vermont, and Washington, while remaining "fully illegal" in 11 states. It is also now permissible under the law of at least 15 states for individuals to grow their own marijuana plants, although in many of these states the home-grow is limited to some sort of authorized medicinal use. It is expected that the wave of legalization will continue to the point of some form of federal legalization or decriminalization.

Typically, marijuana products are available to users for purchase in specialized "dispensaries" that offer dried flower, edibles, tinctures, extracts, and the like. In some cases, a unique or unusual chemical profile, or chemotype, is attractive not only for flower sales but also for use in the preparation of extracts and/or isolates and for the manufacture of a variety of products that possess characteristics of the chemotype.

SUMMARY OF THE INVENTION

The aim for the development of the new *C. sativa* variety, 'V3', was to produce a variety featuring increased THCV levels relative to THC levels. The phytochemicals in *Cannabis* are known for their ability to affect the human body. In live plants, THC is found in the form of tetrahydrocannabolic acid (THCA) that is converted to THC during drying or under high heat. Similarly, THCV in live plants is in the form of tetrahydrocannabivarin carboxylic acid (THCVA). THC and THCV both bind to the cannabinoid receptors 1 ($CB_1$) and 2 ($CB_2$). Binding of $CB_1$ by its endogenous ligands, anandamide or 2-arachidonoylglycerol, stimulates food intake (Silvestri, C., Di Marzo, V. 17 Cell Metabolism 475-490 (2013)). THC acts as an agonist of $CB_1$ and stimulates appetite while THCV is a mild antagonist of $CB_1$ lessens sensations of hunger (Pertwee, R G. 153 British Journal of Pharmacology 199-215 (2008)). The ability of THCV to act as an antagonist of $CB_1$ has led to investigation of using THCV to treat metabolic syndrome and obesity (Riedel, G., et al., 156 British Journal of Pharmacology 1154-1166 (2009)). Selection of a variety producing increased amounts of THCV allows optimized isolation of THCV which may be used in treatment of metabolic syndrome.

Embodiments of the invention relate to a seed from *Cannabis* plant designated 'V3' wherein a representative sample of seed of said plant has been deposited.

Some embodiments of the invention relate to a *Cannabis* plant, or plant part, tissue, or cell thereof produced by growing the seed from *Cannabis* plant designated 'V3', or a descendant thereof.

In some embodiments, the *Cannabis* plant, or plant part, tissue, or cell thereof has a cannabinoid profile set forth in Table 1.

Some embodiments of the invention relate to the use of the plant disclosed herein in a breeding program to produce *Cannabis* progeny with a cannabinoid profile set forth in Table 1 and genetic capacity to produce the cannabinoid profile set forth in Table 1 in progeny thereof.

In some embodiments, the *Cannabis* plant part is selected from stems, trichomes, leaves, or flower buds.

In some embodiments, the invention relates to the *Cannabis* plant descended from the plant, or plant part, tissue, cell or seed of 'V3', wherein the plant is a clonal descendent.

BRIEF DESCRIPTION OF PICTURES

The accompanying photographs show the typical appearance of the new variety 'V3'. The colors are as nearly true as is reasonably possible in a color representation of this type. Colors in the photographs may differ slightly from the color values cited in the detailed botanical description which accurately describes the colors of the new plant.

DETAILED DESCRIPTION

Figure 1:
FIG. 1 is a photograph of the new variety 'V3' at about age 18 weeks in Laytonville, Calif., U.S.A. in a 200-gallon container. The photograph was taken in July 2018.
Figure 2:
FIG. 2 is a photograph of the new variety 'V3' at about age 28 weeks in its flowering stage in Laytonville, Calif., U.S.A. The photograph was taken in October 2018 and demonstrates small bud structure.
Figure 3:
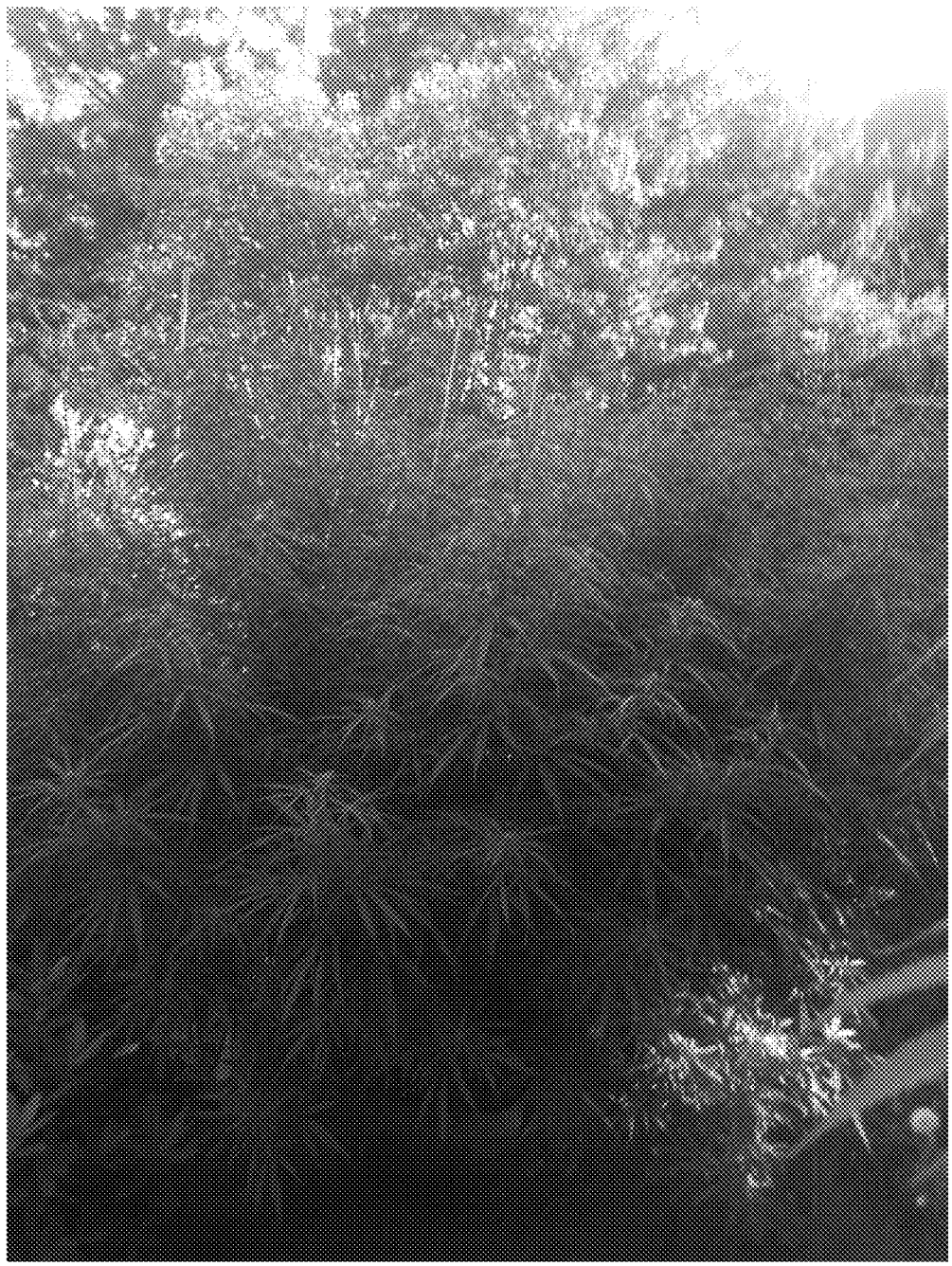
FIG. 3 is a photograph of the new variety 'V3' at about age 28-30 weeks in Laytonville, Calif., U.S.A. The photograph demonstrates the difference in bud structure and maturity with the V3 in background along with clearly different leaf structure of a different variety.
Figure 4:
FIG. 4 is a photograph of the new variety 'V3' at about age 28-30 weeks in its flowering stage in Laytonville, Calif., U.S.A. The photograph was taken in October 2018 and demonstrates bud and leaf structure.
Figure 5:
FIG. 5 is a photograph of the new variety 'V3' at about age 4-6 weeks in Laytonville, Calif., U.S.A. in a greenhouse. The photograph was taken in April/May 2018.

The new *C. sativa* variety is a selection resulting from cross of a female parent F12(P20)' (unpatented) and a male parent 'M31(P20)' (unpatented) in Laytonville, Calif., U.S.A since 2016. The new *C. sativa* variety 'V3' differs from the parental varieties, female F12(P20) and male M31(P20), by having an increased production of THCV.

Plants of the new variety differ from typical *C. sativa* plants in increased production of THCV compared to THC as determined by cannabinoid testing performed by an independent testing service. *C. sativa* 'V3' demonstrates elevated THCVA levels of 4.23% and a total THCV (THCV+THCVA) of up to 4.41% in tested flowers. *C. sativa* 'V3' is a new variety with increased production of THCV compared to standard *C. sativa* varieties. This enhanced production of THCV makes 'V3' a variety of interest for production of medicinal products. 'V3' has elevated levels of the unique terpene, farnesene (0.01-.0.37% or higher). Farnesene is not normally observed in *C. sativa* and this may be a unique identifier of 'V3'.

The selection has been propagated in Laytonville, Calif., U.S.A. Asexual reproduction of the new variety since 2016 has demonstrated that the new variety reproduces true to type with all of the characteristics, as herein described, firmly fixed. Seeds representative of the 'V3' variety have also been produced. The seeds on deposit reflect the key characteristics of the 'V3' variety.

Some embodiments of the invention relate to a seed from a *Cannabis* plant designated 'V3' wherein a representative sample of seed of said plant has been deposited under accession number NCIMB 43868.

Some embodiments of the invention relate to a *Cannabis* plant, or plant part, tissue, or cell thereof produced by growing the seed of 'V3', or a descendant thereof. Plant parts can include the embryo, shoot, root, stem, seed, stipule, leaf, petal, flower bud, flower, ovule, bract, trichome, branch, petiole, internode, bark, pubescence, tiller, rhizome, frond, blade, ovule, pollen, stamen, and the like.

The plants, or plant parts of the invention can display a cannabinoid profile within the ranges as set forth in Table 1, as defined herein. The productivity of any given cannabinoid and/or the amounts or ratios of cannabinoids, terpenes, and other plant products can be, by nature, quite variable. The variability can be contributed to by weather, latitude, soil and feeding conditions, pathogens, and numerous other agronomic, horticultural, and biological factors.

Some embodiments of the invention relate to methods of using the plant in a breeding program to produce cannabis progeny including a cannabinoid profile generally within the ranges as set forth in Table 1. Details of existing *Cannabis* plant varieties and breeding are described in Potter et al. (2011, World Wide Weed: Global Trends in Cannabis Cultivation and Its Control), Holland (2010, The Pot Book: A Complete Guide to *Cannabis,* Inner Traditions/Bear & Co, ISBN1594778981, 9781594 778988), Green I (2009, The *Cannabis* Grow Bible: The Definitive Guide to Growing Marijuana for Recreational and Medical Use, Green Candy Press, 2009, ISBN 1931160589, 9781931160582), Green II (2005, The *Cannabis* Breeder's Bible: The Definitive Guide to Marijuana Genetics, *Cannabis* Botany and Creating Strains for the Seed Market, Green Candy Press, 1931160279, 9781931160278), Starks (1990, Marijuana Chemistry Genetics, Processing & Potency, ISBN 0914171399, 9780914171393), Clarke (1981, Marijuana Botany, an Advanced Study: The Propagation and Breeding of Distinctive *Cannabis,* Ronin Publishing, ISBN 091417178X, 9780914171782), Short (2004, Cultivating Exceptional *Cannabis:* An Expert Breeder Shares His Secrets, ISBN 1936807122, 9781936807123), Cervantes (2004, Marijuana Horticulture: The Indoor/Outdoor Medical Grower's Bible, Van Patten Publishing, ISBN 187882323X, 9781878823236), Franck et al. (1990, Marijuana Grower's Guide, Red Eye Press, ISBN 0929349016, 9780929349015), Grotenhermen and Russo (2002, *Cannabis* and Cannabinoids: Pharmacology, Toxicology, and Therapeutic Potential, Psychology Press, ISBN 0789015080, 9780789015082), Rosenthal (2007, The Big Book of Buds: More Marijuana Varieties from the World's Great Seed Breeders, ISBN 1936807068, 9781936807062), Clarke, R C (*Cannabis:* Evolution and Ethnobotany 2013), King, J (Cannabible Vols 1-3, 2001-2006), and four volumes of Rosenthal's Big Book of Buds series (2001, 2004, 2007, and 2011), each of which is herein incorporated by reference in its entirety for all purposes.

The present invention also relates to variants, mutants and minor modifications of the seeds, plant parts and/or whole plants of the *Cannabis* plants of the present invention. Variants, mutants and minor modifications of the seeds, plants, plant parts, plant cells of the present invention can be generated by methods well known and available to one skilled in the art, including but not limited to, mutagenesis (e.g., chemical mutagenesis, radiation mutagenesis, transposon mutagenesis, insertional mutagenesis, signature tagged mutagenesis, site-directed mutagenesis, and natural mutagenesis), knock-outs/knock-ins, antisense and RNA interference. For more information of mutagenesis in plants, such as agents, protocols, see Acquaah et al. (Principles of plant genetics and breeding, Wiley-Blackwell, 2007, ISBN 1405136464, 9781405136464,) which is herein incorporated by reference in its entirety. Other kinds of modifications practiced in the Cannabis industry, including but not limited to feminization of seeds and/or day-length neutrality/autoflowering are also within the scope of the invention and are within the level of skill in the art to execute.

The present invention also relates to a mutagenized population of the *Cannabis* plants of the present invention, and methods of using such populations. In some embodiments, the mutagenized population can be used in screening for new *Cannabis* lines which comprises one or more or all of the morphological, physiological, biological, and/or chemical characteristics of *Cannabis* plants of the present invention.

In some embodiments, the new *Cannabis* plants obtained from the screening process comprise one or more or all of the morphological, physiological, biological, and/or chemical characteristics of *Cannabis* plants of the present invention, and one or more additional or different new morphological, physiological, biological, and/or chemical characteristic.

The present invention also provides any compositions or any products made from or isolated from the plants of the present invention. In some embodiments, the compositions/ products comprise an extract of the plants. In some embodiments, the extract can contain a higher percentage of terpenes/terpenoids compared to extract isolated from a control *Cannabis* plant variety (e.g., an existing variety, such as a recreational *Cannabis* plant variety). In some embodiments, the invention relates to a smokable or edible product comprising the *Cannabis* plant, or plant part, tissue, cell, extract, or isolate.

The present invention provides methods of using the *Cannabis* plants or any parts, any compositions, or any chemicals derived from said plants of the present invention.

In some embodiments, the plants of the present invention can be used to produce new plant varieties. In some embodiments, the plants are used to develop new varieties or hybrids with desired phenotypes or genotypes.

In some embodiments, selection methods, e.g., molecular marker assisted selection, can be combined with breeding methods to accelerate the process. Additional breeding methods known to those of ordinary skill in the art include, e.g., methods discussed in Chahal and Gosal (Principles and procedures of plant breeding: biotechnological and conventional approaches, CRC Press, 2002, ISBN 084931321X, 9780849313219), Taji et al. (In vitro plant breeding, Routledge, 2002, ISBN 156022908X, 9781560229087), Richards (Plant breeding systems, Taylor & Francis US, 1997, ISBN 0412574500, 9780412574504), Hayes (Methods of Plant Breeding, Publisher: READ BOOKS, 2007, ISBN1406737062, 9781406737066), each of which is incorporated by reference in its entirety. The *Cannabis* genome has been sequenced (Bakel et al., The draft genome and transcriptome of *Cannabis sativa*, Genome Biology, 12(1 0):R102, 2011). Molecular makers for *Cannabis* plants are described in Datwyler et al. (Genetic variation in hemp and marijuana (*Cannabis sativa* L.) according to amplified fragment length polymorphisms, J Forensic Sci. 2006 March; 51(2):371-5.), Pinarkara et al., (RAPD analysis of seized marijuana (*Cannabis sativa* L.) in Turkey, Electronic Journal of Biotechnology, 12(1), 2009), Hakki et al., (Inter simple sequence repeats separate efficiently hemp from marijuana (*Cannabis sativa* L.), Electronic Journal of Biotechnology, 10(4), 2007), Datwyler et al., (Genetic Variation in Hemp and Marijuana (*Cannabis sativa* L.) According to Amplified Fragment Length Polymorphisms, J Forensic Sci, March 2006, 51(2):371-375), Gilmore et al. (Isolation of microsatellite markers in *Cannabis sativa* L. (marijuana), Molecular Ecology Notes, 3(1): 105-107, March 2003), Pacifico et al., (Genetics and marker assisted selection of chemotype in *Cannabis sativa* L.), Molecular Breeding (2006) 17:257-268), and Mendoza et al., (Genetic individualization of *Cannabis sativa* by a short tandem repeat multiplex system, Anal Bioanal Chem (2009) 393:719-726), each of which is herein incorporated by reference in its entirety.

In some embodiments, the *Cannabis* plant, or plant part, tissue, or cell of 'V3' comprises a cannabinoid profile as set forth in Table 1.

TABLE 1

Exemplary Profiles of Key Cannabinoids.

|  | Percent | Percent | Percent | Percent | Percent |
|---|---|---|---|---|---|
| d9-THC | 0.02 | 0.03 | 0.05 | 0.08 | 0.10 |
| THCA | 1.88 | 2.81 | 4.65 | 6.70 | 8.04 |
| Total THC* | 1.67 | 2.50 | 4.13 | 5.96 | 7.15 |
| THCV | 0.00 | 0.01 | 0.03 | 0.18 | 0.22 |
| THCVA | 1.37 | 1.94 | 2.88 | 4.23 | 5.08 |
| THCV + THCVA | 1.37 | 1.95 | 2.91 | 4.41 | 5.30 |

TABLE 1-continued

Exemplary Profiles of Key Cannabinoids.

|  | Percent | Percent | Percent | Percent | Percent |
|---|---|---|---|---|---|
| CBG + CBGA | 0.16 | 0.28 | 0.58 | 1.03 | 1.24 |
| CBCA | 0.05 | 0.07 | 0.12 | 0.37 | 0.45 |
| Total Cannabinoid | 3.25 | 4.80 | 7.77 | 12.04 | 14.45 |
| THCV/THC (%) | 82 | 78 | 70 | 74 | 74 |
| THCV/Total Cannabinoid (%) | 42 | 40 | 37 | 37 | 37 |

*Total THC = (THCA * 0.877) + THC (i.e. delta 9 THC) + delta 8 THC

In some embodiments, the invention relates to a *Cannabis* clone regenerated from the *Cannabis* plant of descended from the plant, or plant part, tissue, cell or seed of 'V3' wherein the plant is a clonal descendent.

In some embodiments, the invention relates to a method of producing an F1 *Cannabis* seed, wherein the method includes crossing the plant with a different *Cannabis* plant and harvesting the resultant F1 cannabis seed. In some embodiments, the invention relates to the F1 hybrid cannabis seed produced by this method. In some embodiments, the invention relates to a F1 hybrid *Cannabis* plant produced by growing the F1 hybrid cannabis seed. In some embodiments, the invention relates to a cannabis clone regenerated from the F1 hybrid *Cannabis* plant. In some embodiments, the invention relates to a smokable or edible product comprising cannabis tissue from the F1 hybrid *Cannabis* plant.

The following detailed description sets forth the distinctive characteristics of 'V3'. Applicant is prepared to make a deposit of seeds or plant tissue.

Type: Herbaceous tap-rooted annual.
Classification:
 a. Family—Cannabaeae.
 b. Genus—*Cannabis*.
 c. Species—*sativa*.
 d. Common Name—marijuana.
Parentage: Female Parent—F12(P20); Male Parent—'M31(P20)'
Market Class: A medicinal herb intended for use as medical oil, and medicinal herb for sale in cannabis dispensaries 'and for use in the manufacture of medicinal and recreational products.

GENETIC ANALYSIS

A genetic analysis was conducted on a tissue sample of 'V3'. The results of the analysis are as follows:
A. Closest Known Relatives in Reference Genetic Database:
 'V1' aka EJN3, which is the subject matter of provisional patent application 62/832,846, filed on Apr. 11, 2019, entitled "CANNABIS PLANT NAMED 'V1'", as well as applications for plant patent and utility patent claiming priority therefrom.
 'V2' aka Masai, which is the subject matter of provisional patent application 62/832,859, filed on Apr. 11, 2019, entitled "CANNABIS PLANT NAMED 'V2'", as well as applications for plant patent and utility patent claiming priority therefrom.
 'Durban Poison' a popular, unpatented variety believed to have originated in the area of Durban, South Africa.
B. Population Profile:
 'V3' was indicated to have genetic heritage similar to varieties in "Landrace" subpopulations with minor similarities to "Skunk" and "CBD" subpopulations.

C. Genotypic Combination Analysis

'V3' was found to have a genotypic combination that would be classified as "rare."

D. Genetic Variation (Heterozygosity) Analysis

'V3' was found to have a moderate level of heterozygosity as compared with other varieties in the reference database.

DEPOSIT INFORMATION

A seed sample of this invention has been deposited with an International Depositary Authority as established under the Budapest Treaty according to 37 CFR 1.803(a)(1), at the National Collections of Industrial, Food and Marine Bacteria Ltd. (NCIMB) in Aberdeen Scotland under NCIMB No. 43868.

To satisfy the enablement requirements of 35 U.S.C. 112, and to certify that the deposit of the *Cannabis* varieties of the present invention meets the criteria set forth in 37 CFR 1.801-1.809 and Manual of Patent Examining Procedure (MPEP) 2402-2411. 05, Applicant(s) hereby makes the following statements regarding the deposited cannabis variety: If the deposit is made under the terms of the Budapest Treaty, the instant invention will be irrevocably and without restriction released to the public upon the granting of a patent. If the deposit is made not under the terms of the Budapest Treaty, Applicant(s) provides assurance of compliance by the following statements:

1. During the pendency of this application, access to the invention will be afforded to the Commissioner upon request;
2. All restrictions on availability to the public will be irrevocably removed upon granting of the patent under conditions specified in 37 CFR 1.808;
3. The deposit will be maintained in a public repository for a period of 30 years or 5 years after the last request or for the effective life of the patent, whichever is longer;
4. A test of the viability of the biological material at the time of deposit will be conducted by the public depository under 37 CFR 1.807; and
5. The deposit will be replaced if it should ever become unavailable.

Access to this deposit will be available during the pendency of this application to persons determined by the Commissioner of Patents and Trademarks to be entitled thereto under 37 C.F.R. § 1.14 and 35 U.S.C. § 122. Upon granting of any claims in this application, all restrictions on the availability to the public of the variety will be irrevocably and without restriction or condition removed by affording access to a deposit of the tissue sample of the same variety with the depository.

The invention claimed is:

1. A seed from *Cannabis* plant designated 'V3' wherein a representative sample of seed of said plant has been deposited under accession number NCIMB 43868; wherein flower produced from *Cannabis* plant, or plant part, tissue, or cell thereof comprises a cannabinoid profile of:
   a. d9-THC between 0.02%-0.10%;
   b. THCA between 1.88%-8.04%;
   c. Total THC between 1.67%-7.15%;
   d. THCV between 0%-0.22%;
   e. THCVA between 1.37%-5.08%;
   f. THCV+THCVA between 1.37%-5.30%;
   g. CBG+CBGA between 0.16%-1.24%;
   h. CBCA between 0.05%-0.45%;
   i. Total cannabinoid between 3.25%-14.45%;
   j. THCV/THC between 82%-74%; and
   k. THCV/Total cannabinoid between 42%-37%.

2. A *Cannabis* plant, or plant part, tissue, or cell thereof produced by growing the seed of claim 1, or a descendant thereof; wherein flower produced from *Cannabis* plant, or plant part, tissue, or cell thereof comprises a cannabinoid profile of:
   a. d9-THC between 0.02%-0.10%;
   b. THCA between 1.88%-8.04%;
   c. Total THC between 1.67%-7.15%;
   d. THCV between 0%-0.22%;
   e. THCVA between 1.37%-5.08%;
   f. THCV+THCVA between 1.37%-5.30%;
   g. CBG+CBGA between 0.16%-1.24%;
   h. CBCA between 0.05%-0.45%;
   i. Total cannabinoid between 3.25%-14.45%;
   j. THCV/THC between 82%-74%; and
   k. THCV/Total cannabinoid between 42%-37%.

3. The *Cannabis* plant, or plant part, tissue, or cell thereof of claim 2, wherein flower produced from the plant comprises comprising a cannabinoid profile of:
   a. d9-THC between 0.02%-0.10%;
   b. THCA between 1.88%-8.04%;
   c. Total THC between 1.67%-7.15%;
   d. THCV between 0%-0.22%;
   e. THCVA between 1.37%-5.08%;
   f. THCV+THCVA between 1.37%-5.30%;
   g. CBG+CBGA between 0.16%-1.24%;
   h. CBCA between 0.05%-0.45%;
   i. Total cannabinoid between 3.25%-14.45%;
   j. THCV/THC between 82%-74%; and
   k. THCV/Total cannabinoid between 42%-37%.

4. The *Cannabis* plant part of claim 2, wherein said plant part is selected from the group consisting of: stems, trichomes, leaves, and flower buds.

5. The *Cannabis* plant descended from the plant, or plant part, tissue, cell or seed of claim 2, wherein the plant is a clonal descendent.

6. A method of breeding a *Cannabis* plant, or plant part, tissue, or cell thereof, wherein the plant, plant part, tissue, or cell is produced by growing a seed or clone from:
   a. a *Cannabis* plant designated 'V3' wherein a representative sample of seed of said plant has been deposited under accession number NCIMB 43868; or
   b. a descendant of the Cannabis plant designated 'V3'. wherein the plant comprises a cannabinoid profile of:
   a. d9-THC between 0.02%-0.10%;
   b. THCA between 1.88%-8.04%;
   c. Total THC between 1.67%-7.15%;
   d. THCV between 0%-0.22%;
   e. THCVA between 1.37%-5.08%;
   f. THCV+THCVA between 1.37%-5.30%;
   g. CBG+CBGA between 0.16%-1.24%;
   h. CBCA between 0.05%-0.45%;
   i. Total cannabinoid between 3.25%-14.45%;
   j. THCV/THC between 82%-74%; and
   k. THCV/Total cannabinoid between 42%-37%; and wherein the method comprises providing the plant as at least one parent in a breeding program and selecting progeny displaying the cannabinoid profile of:
   a. d9-THC between 0.02%-0.10%;
   b. THCA between 1.88%-8.04%;
   c. Total THC between 1.67%-7.15%;
   d. THCV between 0%-0.22%;
   e. THCVA between 1.37%-5.08%;
   f. THCV+THCVA between 1.37%-5.30%;
   g. CBG+CBGA between 0.16%-1.24%;

h. CBCA between 0.05%-0.45%;
i. Total cannabinoid between 3.25%-14.45%;
j. THCV/THC between 82%-74%; and
k. THCV/Total cannabinoid between 42%-37%.

\* \* \* \* \*